United States Patent
Lewallen

(10) Patent No.: US 8,858,634 B2
(45) Date of Patent: Oct. 14, 2014

(54) SOFT TISSUE ATTACHMENT DEVICE

(75) Inventor: David G. Lewallen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 903 days.

(21) Appl. No.: 12/612,205

(22) Filed: Nov. 4, 2009

(65) Prior Publication Data

US 2010/0114127 A1    May 6, 2010

Related U.S. Application Data

(60) Provisional application No. 61/111,051, filed on Nov. 4, 2008.

(51) Int. Cl.
*A61F 2/08* (2006.01)

(52) U.S. Cl.
CPC ....... *A61F 2/0811* (2013.01); *A61F 2002/0888* (2013.01); *A61F 2002/0858* (2013.01); *A61F 2002/0864* (2013.01); *A61F 2002/0829* (2013.01)
USPC .......................... 623/13.14; 606/300; 606/151

(58) Field of Classification Search
CPC ........... A61F 2/0811; A61F 2002/0817; A61F 2002/0823; A61F 2002/0841; A61F 2002/0847
USPC ............ 623/13.14, 13.17; 606/300–304, 151, 606/324, 328
See application file for complete search history.

(56) References Cited

U.S. PATENT DOCUMENTS

| | | | |
|---|---|---|---|
| 2,180,866 A | 11/1939 | Cryer | |
| 3,855,638 A | 12/1974 | Pilliar | |
| 4,206,516 A | 6/1980 | Pilliar | |
| 5,024,669 A | 6/1991 | Peterson et al. | |
| 5,269,784 A * | 12/1993 | Mast | 606/288 |
| 5,282,861 A | 2/1994 | Kaplan | |
| 5,734,959 A | 3/1998 | Krebs et al. | |
| 5,931,869 A | 8/1999 | Boucher et al. | |
| 6,554,862 B2 | 4/2003 | Hays et al. | |
| 6,746,483 B1 | 6/2004 | Bojarski et al. | |
| 6,749,639 B2 | 6/2004 | Lewallen | |
| 6,945,448 B2 | 9/2005 | Medlin et al. | |
| 7,208,222 B2 | 4/2007 | Rolfe et al. | |
| 7,255,700 B2 * | 8/2007 | Kaiser et al. | 606/304 |
| 2007/0162022 A1 | 7/2007 | Zhang et al. | |

OTHER PUBLICATIONS

Reach et al., Direct Tendon Attachment and Healing to Porous Tantalum: An Experimental Animal Study, J Bone Joint Surg Am. 2007; 89:1000-1009.

* cited by examiner

*Primary Examiner* — Thomas J Sweet
*Assistant Examiner* — Christopher D Prone
(74) *Attorney, Agent, or Firm* — Quarles & Brady, LLP

(57) ABSTRACT

Methods and devices are disclosed for the attachment of a soft tissue structure (e.g., tendon or ligament) to bone or a prosthetic implant. In one form, the device includes a clamp having a convex tissue engaging surface. A fastener compresses the soft tissue between the tissue engaging surface and the bone or the prosthetic implant. In another form, the device includes a second clamp comprising a porous metallic material. The second clamp has a first surface, a concave tissue engaging surface opposite the first surface, and a throughhole for a fastener. The second clamp is placed adjacent the bone, the soft tissue is placed adjacent the second clamp, and the first clamp is placed adjacent the soft tissue. The soft tissue is compressed between the convex tissue engaging surface of the first clamp and the concave tissue engaging surface of the second clamp using the fastener.

11 Claims, 6 Drawing Sheets

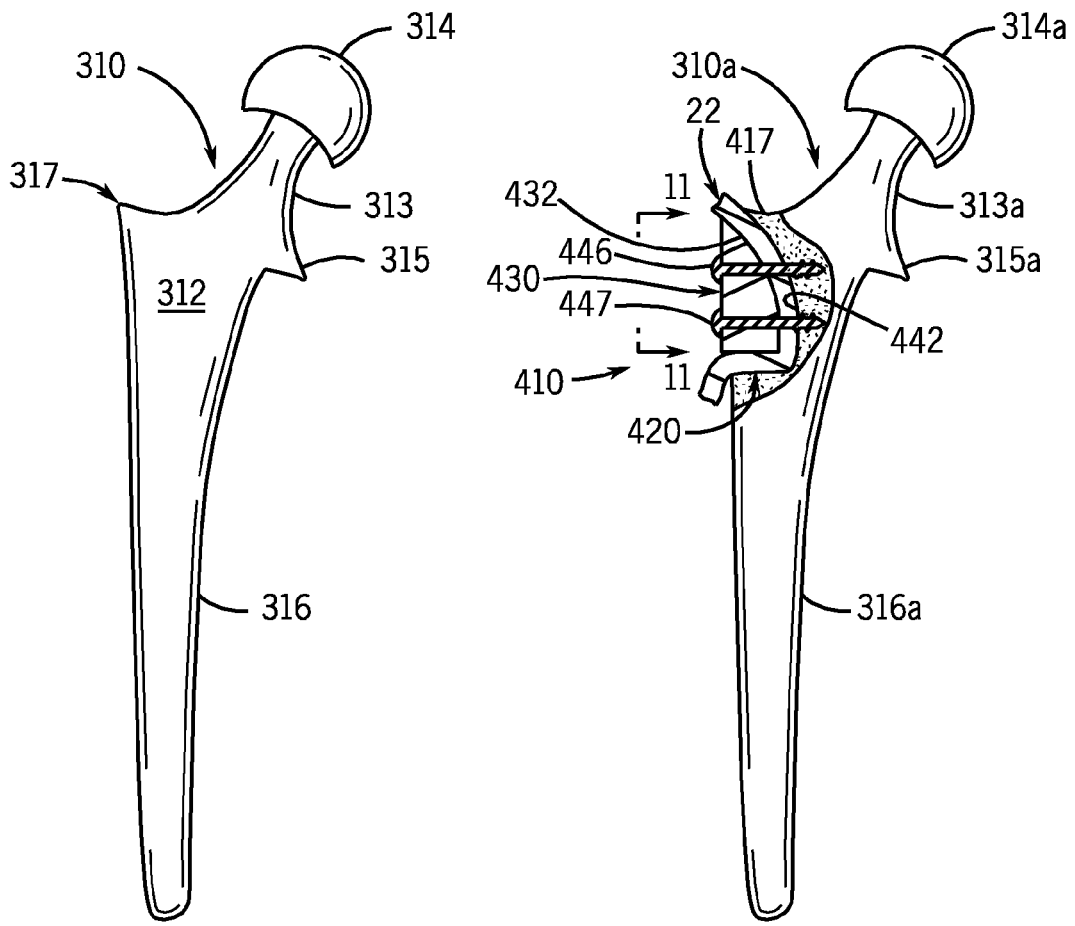
FIG. 9
PRIOR ART
FIG. 10
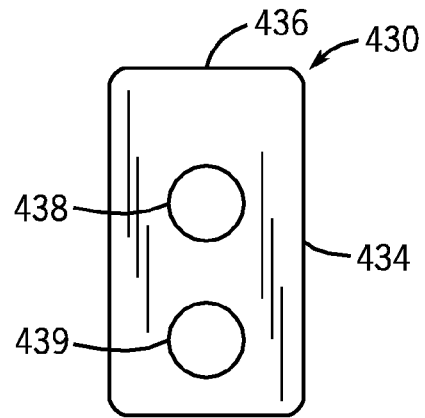
FIG. 11

SOFT TISSUE ATTACHMENT DEVICE

CROSS-REFERENCES TO RELATED APPLICATIONS

This application claims priority based on U.S. Provisional Application No. 61/111,051 filed Nov. 4, 2008.

STATEMENT REGARDING FEDERALLY SPONSORED RESEARCH

Not Applicable.

BACKGROUND OF THE INVENTION

1. Field of the Invention

The invention relates to methods and devices for the attachment of a tendon or ligament structure to bone and/or a prosthetic implant (such as a joint replacement device). In particular, the methods and devices use a clamping strategy employing soft tissue healing to a porous metal clamp.

2. Description of the Related Art

Surgical techniques in which a tendon is fixed directly to bone have been successful in achieving a strong tendon-bone attachment in selected circumstances. However, when tendon is directly fixed to metallic implants, weak fixation and mechanical failure under physiologic loading have been observed.

It has been shown that porous tantalum can function as a soft-tissue attachment and repair biomaterial. In "Direct Tendon Attachment and Healing to Porous Tantalum: An Experimental Animal Study", *The Journal Of Bone And Joint Surgery*, 2007; 89:1000-9, an animal model was used to demonstrate the potential utility of porous metals to achieve healing of tendon directly to a porous metallic device. Example ligament attachment devices can also be found in U.S. Pat. No. 7,208,222 and U.S. Patent Application Publication No. 2007/0162022.

Still, there exists a need for improved methods and devices for the attachment of a tendon or ligament structure to bone or a prosthetic implant.

SUMMARY OF THE INVENTION

The present invention addresses the foregoing needs by providing porous metal (such as tantalum or titanium) devices to attach (via screw or screws) soft tissue (tendons or ligaments) to bone or to prosthetic implants. Porous metal allows the ingrowth of soft tissue. The attachment devices of the invention can allow varying degrees of soft tissue compression due to the difference in curvature of (i) a first convex clamp and (ii) a second concave clamp, or a concave depression in bone or an implant. Compression of a tendon or ligament between a concave porous ingrowth surface on one side, and a convex surface of smaller radius of curvature on the other allows for varying degrees of compression. In other words, the gap between the concave porous ingrowth surface on one side and the convex surface on the other side gets bigger near the outer edge of the clamp or depression and is smallest centrally.

Because tendons and ligaments are of different thicknesses and have different requirements for clamping tension, having varying degrees of compression in the invention increases the likelihood that at some point along the curvature of the clamp(s), the level of compression would be optimal for ingrowth of soft tissue and implant success rates would increase. Also, compression across the soft tissue-clamp interface at varying degrees negates needing to find perfect tension. As a result, soft tissue ingrowth into metal is achieved because compression is just right. Furthermore, the soft tissue is flat in the center of the clamp.

In one aspect, the invention provides a device for attaching soft tissue to a bone or a prosthetic implant. The device includes a clamp and a fastener. The clamp comprises a porous metallic material, and the clamp includes a first surface, a convex tissue engaging surface opposite the first surface, and a throughhole extending from the first surface to the convex tissue engaging surface. The fastener is dimensioned for placement in the throughhole, and the fastener is dimensioned to engage the first surface, the soft tissue and the bone or the prosthetic implant such that the soft tissue is compressed between the tissue engaging surface and the bone or the prosthetic implant.

In one form, the convex tissue engaging surface of the clamp has a first curvature, the bone or the prosthetic implant includes a depression of a second curvature, and the first curvature is greater than the second curvature. The convex tissue engaging surface of the clamp can be dome shaped. A grommet can be arranged in the throughhole. The convex tissue engaging surface of the clamp can include a raised section around the throughhole. The clamp can include a second throughhole for receiving a second fastener. Various shapes are suitable for the clamp. For example, the clamp can include a periphery having a shape selected from circular, rectangular, elliptical and oval.

The device can include a second clamp comprising a porous metallic material. The second clamp can include a first part and a mating second part wherein the soft tissue is compressed between the first part and the second part. In one form, the first part comprises a first channel, the second part comprises a second channel, and the soft tissue is compressed between an inner surface of the first channel of the first part and an inner surface of the second channel of the second part. The first part and the second part can form a frustoconical shape when mated together.

In another aspect, the invention provides a device for attaching soft tissue to a bone or a prosthetic implant. The device includes a first clamp, a second clamp, and a fastener. The first clamp comprises a porous metallic material. The first clamp includes a first surface, a convex tissue engaging surface opposite the first surface, and a throughhole extending from the first surface to the convex tissue engaging surface of the first clamp. The convex tissue engaging surface of the first clamp can be dome shaped. The second clamp comprises a porous metallic material. The second clamp includes a first surface, a concave tissue engaging surface opposite the first surface, and a throughhole extending from the first surface to the concave tissue engaging surface of the second clamp. The fastener is dimensioned for placement in the throughhole of the first clamp and the throughhole of the second clamp. The fastener is dimensioned to engage the first surface of the first clamp, the soft tissue and the bone or the prosthetic implant such that the soft tissue is compressed between the convex tissue engaging surface of the first clamp and the concave tissue engaging surface of the second clamp.

In one form, the convex tissue engaging surface of the first clamp has a first curvature, the concave tissue engaging surface of the second clamp has a second curvature, and the first curvature is greater than the second curvature. The first clamp can include a periphery having a shape selected from circular, rectangular, elliptical and oval, and the second clamp can include a periphery having a shape selected from circular, rectangular, elliptical and oval. In one use of the device, a depression is formed in a bone, and the second clamp is received in the depression of the bone. The porous metallic material of the first clamp can be tantalum, and the porous metallic material of the second clamp can be tantalum.

In yet another aspect, the invention provides a method for attaching soft tissue to a bone. The method uses a clamp comprising a porous metallic material wherein the clamp includes a first surface, a convex tissue engaging surface opposite the first surface, and a throughhole extending from the first surface to the convex tissue engaging surface. The soft tissue is placed adjacent the bone, and the clamp is placed adjacent the soft tissue opposite the bone. A fastener is inserted through the throughhole, through the soft tissue and into the bone such that the soft tissue is compressed between the tissue engaging surface and the bone. The convex tissue engaging surface of the clamp can have a first curvature, and the method can further comprise forming a depression of a second curvature in the bone, wherein the first curvature of the convex tissue engaging surface of the clamp is greater than the second curvature of the depression. The soft tissue is placed in the depression such that the soft tissue is compressed between the convex tissue engaging surface and the bone.

In still another aspect, the invention provides a method for attaching soft tissue to a prosthetic implant. The method uses a clamp comprising a porous metallic material. The clamp includes a first surface, a convex tissue engaging surface opposite the first surface, and a throughhole extending from the first surface to the convex tissue engaging surface. The soft tissue is placed adjacent the prosthetic implant, and the clamp is placed adjacent the soft tissue opposite the implant. A fastener is inserted through the throughhole, through the soft tissue and into the prosthetic implant such that the soft tissue is compressed between the tissue engaging surface and the prosthetic implant. The convex tissue engaging surface of the clamp can have a first curvature, and the prosthetic implant can further comprise a depression of a second curvature in the prosthetic implant, wherein the first curvature of the convex tissue engaging surface of the clamp is greater than the second curvature of the depression. The soft tissue is placed in the depression such that the soft tissue is compressed between the convex tissue engaging surface and the prosthetic implant.

In yet another aspect, the invention provides a method for attaching soft tissue to a bone. The method uses a first clamp comprising a porous metallic material and a second clamp comprising a porous metallic material. The first clamp includes a first surface, a convex tissue engaging surface opposite the first surface, and a throughhole extending from the first surface to the convex tissue engaging surface. The second clamp includes a first surface, a concave tissue engaging surface opposite the first surface, and a throughhole extending from the first surface to the concave tissue engaging surface. The second clamp is placed adjacent the bone, and the soft tissue is placed adjacent the second clamp opposite the bone. The first clamp is placed adjacent the soft tissue opposite the second clamp, and a fastener is inserted through the throughhole of the first clamp, through the soft tissue, through the throughhole of the second clamp and into the bone such that the soft tissue is compressed between the convex tissue engaging surface of the first clamp and the concave tissue engaging surface of the second clamp. The convex tissue engaging surface of the first clamp can have a first curvature, and the concave tissue engaging surface of the second clamp can have a second curvature, wherein the first curvature is greater than the second curvature.

It is therefore an advantage of the invention to provide improved methods and devices for the attachment of a tendon or ligament structure to bone or to a prosthetic implant.

These and other features, aspects, and advantages of the present invention will become better understood upon consideration of the following detailed description, drawings, and appended claims.

BRIEF DESCRIPTION OF THE DRAWINGS

FIG. 9 is a side view of a prior art femoral prosthesis.

FIG. 10 is a side view, partially in cross-section, of a femoral prosthesis including still another attachment device according to the invention.

FIG. 11 is a lateral view taken along line 11-11 of FIG. 10.

Like reference numerals will be used to refer to like parts from Figure to Figure in the following description of the drawings.

DETAILED DESCRIPTION OF THE INVENTION

Figure 1:
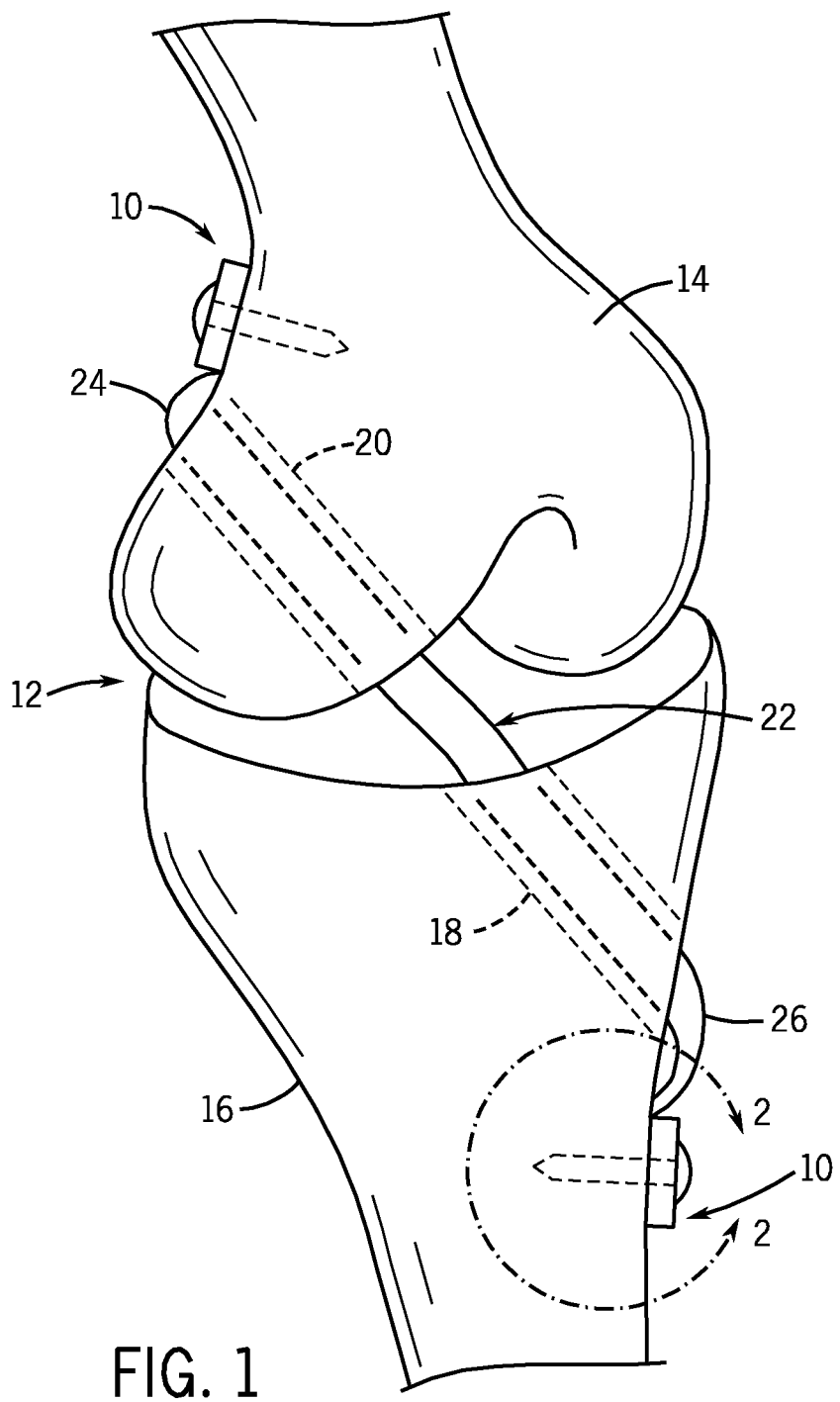
FIG. 1 is a perspective view of a human knee having a ligament attached to the femur and the tibia using an attachment device according to the invention.

Looking first at FIG. 1, there is shown an example application of an attachment device 10 according to the invention in a human knee. This is shown for illustrative purposes, and the attachment device is not limited to knee surgery. The attachment device 10 can be used to attach any soft tissue (such as tendons and ligaments) to any bone. In FIG. 1, the knee joint 12 is shown with femur 14, tibia 16, tibial tunnel 18 and femoral tunnel 20. The tibial tunnel 18 and the femoral tunnel 20 can be prepared using standard techniques. A ligament replacement 22 is arranged in the tibial tunnel 18 and the femoral tunnel 20. A top end 24 of the ligament replacement 22 is attached to the femur 14 using the attachment device 10 and a bottom end 26 of the ligament replacement 22 is attached to the tibia 16 using the attachment device 10.

Figure 2:
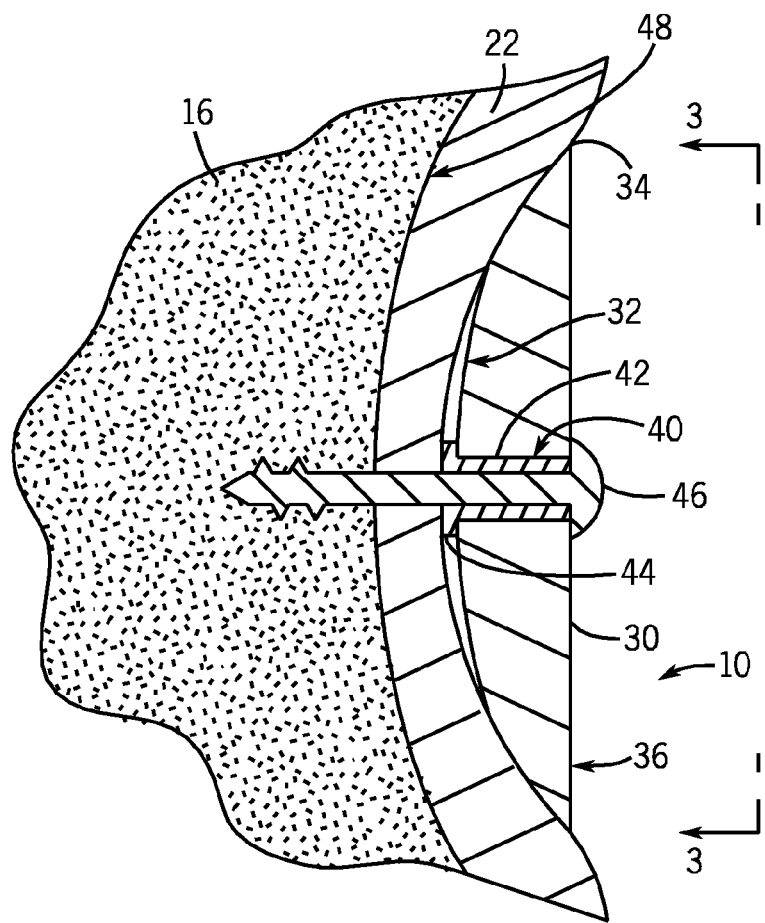
FIG. 2 is a detailed cross-sectional view of the attachment device according to the invention taken along line 2-2 of FIG. 1.
Figure 3:
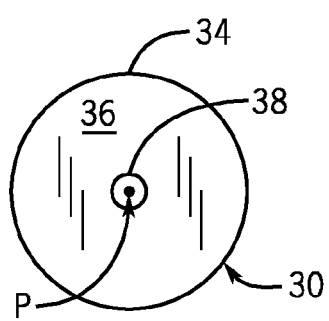
FIG. 3 is a lateral view taken along line 3-3 of FIG. 2.

Turning to FIGS. 2 and 3, the attachment device 10 is shown in greater detail. The attachment device 10 includes a clamp 30 having a domed (convex) tissue engaging surface 32, a circular periphery 34, a bottom surface 36, and a central throughhole 38. A tubular grommet 40 is arranged in the throughhole 38. The side wall 42 of the grommet 40 can engage the inner surface of the throughhole 38 and a flange 44 extends outwardly from an end of the side wall 42. The grommet 40 is optional, but can be advantageous as the grommet 40 can prevent the ligament replacement 22 at the apex of the clamp 30 from being totally flattened. The attachment device 10 also includes a fastener such as screw 46 that is inserted through the grommet 40, through the ligament replacement 22, and into the tibia 16. The screw 46 compresses the ligament replacement 22 between the clamp 30 and the tibia 16. Note in FIG. 2 how the gap between the convex porous ingrowth surface 32 on one side and the concave surface of the depression 48 on the other side gets bigger near the periphery 34 of the clamp 30 and is smallest centrally near screw 46.

In an alternative embodiment, the grommet 40 is omitted and the convex tissue engaging surface 32 includes a raised section around the throughhole 38. This raised section can have an annular shape equivalent to the flange 44 of the grommet 40. This raised section can prevent the ligament replacement 22 at the apex of the clamp 30 from being totally flattened.

The tissue engaging surface 32 of the clamp 30 has a first curvature which can be calculated as the inverse of the radius from a point P (which is on the central axis of the throughhole 38 and which is in the plane of the bottom surface 36) to various points on the tissue engaging surface 32. The ligament replacement 22 is secured between the tissue engaging surface 32 and a depression 48 that can be formed in the tibia 16. The depression 48 has a second curvature which can be calculated as the inverse of the radius from point P (which is on the central axis of the throughhole 38a and which is in the plane of the bottom surface 36) to various points on the inner surface of the depression 48. Also, the depression 48 can be prepared with a depth such that the flat bottom surface 36 of the clamp 30 can be counter-sunk into the tibia 16 if desired.

The clamp 30 and the grommet 40 may comprise a material that promotes soft tissue ingrowth from the ligament replacement 22 into the clamp 30 and the grommet 40. One non-limiting example material is a porous metallic material, also known as metal foam, which can be produced with interconnective porosity coupled with a regular pore shape and size. One such material that is currently commercially available for a variety of orthopedic implants involves the elemental metal tantalum fabricated with >80% interconnective porosity with use of a metal vapor deposition technique (Trabecular Metal from Zimmer, Warsaw, Ind., USA). This material is also described in U.S. Pat. No. 5,282,861 which is incorporated herein by reference. While tantalum is one example porous metallic material, other non-limiting example porous metallic materials include titanium alloys, cobalt-chromium alloys, stainless steel alloys, tantalum alloys, and niobium alloys. The screw 46 is preferably formed from a non-porous metallic material such as a titanium alloy or a stainless steel alloy.

Still referring to FIGS. 2 and 3, it can be seen that the first curvature of the convex tissue engaging surface 32 of the clamp 30 is greater than the second curvature of the depression 48 in the tibia 16. Stated in another way, the radius curvature of the convex tissue engaging surface 32 of the clamp 30 is smaller than the radius of curvature of the depression 48 in the tibia 16. This allows for varying degrees of ligament replacement 22 compression due to the difference in curvature of the first curvature of the convex tissue engaging surface 32 of the clamp 30 and the second curvature of the depression 48 in the tibia 16. As tendons and ligaments are of different thicknesses and have different requirements for tension between the clamp 30 and the tibia 16, having varying degrees of compression between the clamp 30 and the tibia 16 increases the likelihood that at some point along the convex tissue engaging surface 32 of the clamp 30, the level of compression would be optimal for ingrowth of soft tissue and therefore implant success rates increase.

Figure 4:
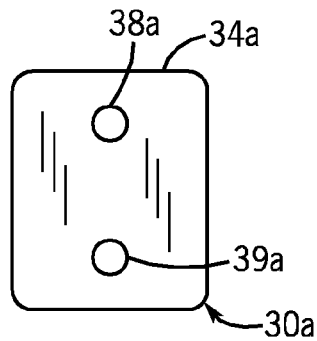
FIG. 4 is a lateral view similar to FIG. 3 showing another version of an attachment device according to the invention.

Turning to FIG. 4, an alternative embodiment of the clamp of the attachment device is shown. The clamp 30a has a generally rectangular periphery 34a, and two throughholes 38a and 39a, which allow for the use of two screws and optionally two grommets. The use of two screws for compressing the ligament replacement 22 between the clamp 30a and the tibia 16 can increase compression force on the ligament replacement 22. The rectangular periphery 34a of the clamp 30a can provide for increased surface area for soft tissue ingrowth. The clamp 30a can comprise the porous metallic materials mentioned above. The convex tissue engaging surface of the clamp 30a can have a radius curvature similar to the radius of curvature of the convex tissue engaging surface 32 of the clamp 30 shown in FIG. 2.

Figure 5:
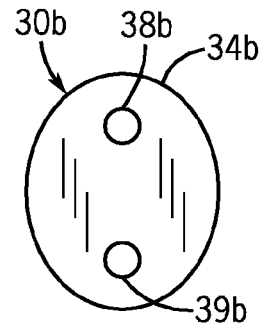
FIG. 5 is a lateral view similar to FIG. 3 showing yet another version of an attachment device according to the invention.

Turning to FIG. 5, another alternative embodiment of the clamp of the attachment device is shown. The clamp 30b has a generally oval periphery 34b, and two throughholes 38b and 39b, which allow for the use of two screws and optionally two grommets. The use of two screws for compressing the ligament replacement 22 between the clamp 30b and the tibia 16 can increase compression force on the ligament replacement 22. The oval periphery 34b of the clamp 30b can provide for increased surface area for soft tissue ingrowth. The clamp 30b can comprise the porous metallic materials mentioned above. The convex tissue engaging surface of the clamp 30b can have a radius curvature similar to the radius of curvature of the convex tissue engaging surface 32 of the clamp 30 shown in FIG. 2.

Figure 6:
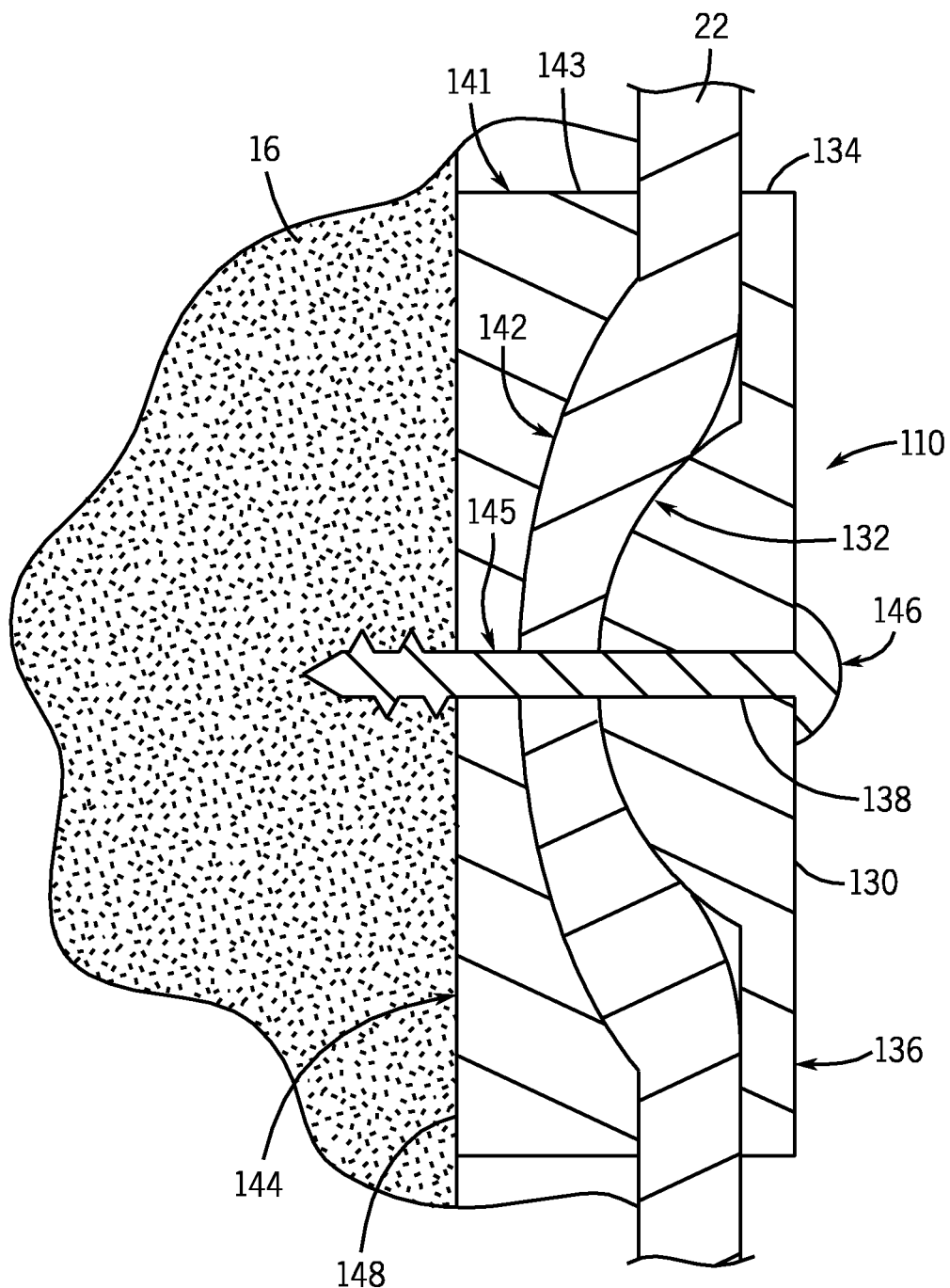
FIG. 6 a detailed cross-sectional view similar to FIG. 2 showing still another version of an attachment device according to the invention.

Looking now at FIG. 6, there is shown another embodiment of an attachment device 110 according to the invention. The attachment device 110 includes a first clamp 130 having a domed (convex) tissue engaging surface 132, a circular periphery 134, a bottom surface 136, and a central throughhole 138. The attachment device 110 also includes a second clamp 141 having a concave tissue engaging surface 142 in a well, a circular periphery 143, a bottom surface 144, and a central throughhole 145. The attachment device 110 also includes a fastener such as screw 146 that is inserted through the throughhole 138, through the ligament replacement 22, through the throughhole 145, and into the tibia 16. The screw 146 compresses the ligament replacement 22 between the first clamp 130 and the second clamp 141, which can be inserted in a circular depression 148 formed in the tibia 16. While the first clamp 130 shown has a circular periphery 134 and the second clamp 141 shown has a circular periphery 143, the periphery of each of the first clamp 130 and the second clamp 141 can have different shapes such as shown in FIGS. 4 and 5.

The tissue engaging surface 132 of the first clamp 130 has a first curvature which can be calculated as the inverse of the radius from a point (which is on the central axis of the throughhole 138 and which is in the plane of the bottom surface 136) to various points on the tissue engaging surface 132. The concave tissue engaging surface 142 of the second clamp 141 has a second curvature which can be calculated as the inverse of the radius from a point (which is on the central axis of the throughhole 138 and which is in the plane of the bottom surface 136) to various points on the concave tissue engaging surface 142 of the second clamp 141.

The first curvature of the convex tissue engaging surface 132 of the clamp 130 is greater than the second curvature of the concave tissue engaging surface 142 of the second clamp 141. Stated in another way, the radius curvature of the convex tissue engaging surface 132 of the clamp 130 is smaller than the radius of curvature of the concave tissue engaging surface 142 of the second clamp 141. This allows for varying degrees of ligament replacement 22 compression due to the difference in curvature of the first curvature of the convex tissue engaging surface 132 of the clamp 130 and the second curvature of the concave tissue engaging surface 142 of the second clamp 141. Note in FIG. 6 how the gap between the convex porous ingrowth surface 132 on one side and the concave tissue engaging surface 142 of the second clamp 141 on the other side gets bigger near the periphery 134 of the clamp 130 and is smallest centrally near screw 146. As tendons and ligaments are of different thicknesses and have different requirements for tension between the first clamp 130 and the second clamp 141, having varying degrees of compression between the first clamp 130 and the second clamp 141 increases the likelihood that at some point along the convex tissue engaging surface 132 of the first clamp 130 and the concave tissue engaging surface 142 of the second clamp 141, the level of compression would be optimal for ingrowth of soft tissue and therefore implant success rates increase.

The first clamp 130 and the second clamp 141 may comprise a material that promotes soft tissue ingrowth from the ligament replacement 22 into first clamp 130 and the second clamp 141 The first clamp 130 and the second clamp 141 can comprise the porous metallic materials mentioned above for clamp 30.

Figure 8:
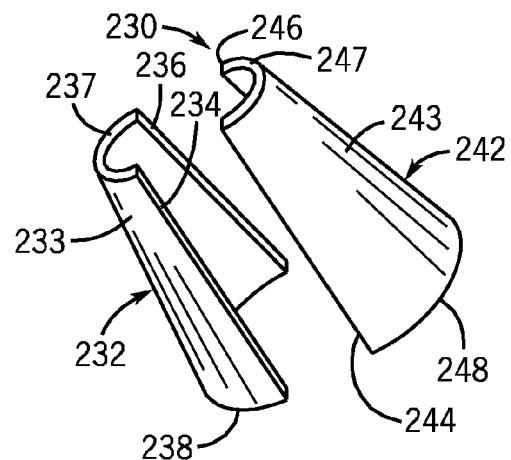
FIG. 8 is a perspective view showing an attachment device of FIG. 7.
Figure 7:
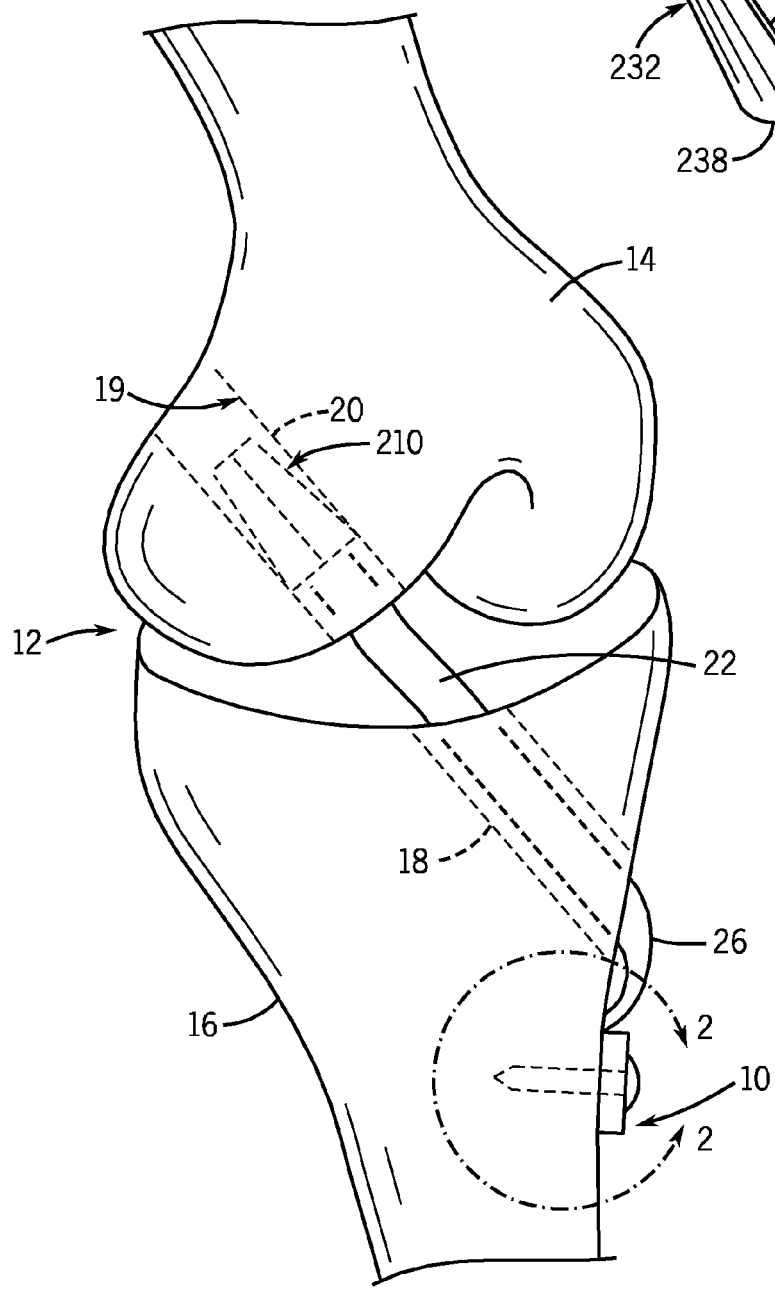
FIG. 7 is a perspective view of a human knee having a ligament attached to the femur and the tibia using yet another version of an attachment device according to the invention.

Turning now to FIGS. 7 and 8, the knee joint 12 is shown with femur 14, tibia 16, tibial tunnel 18 and femoral tunnel 20. The tibial tunnel 18 and the femoral tunnel 20 can be prepared using standard techniques. A ligament replacement 22 is arranged in the tibial tunnel 18 and the femoral tunnel 20. A top end of the ligament replacement 22 is attached to the femur 14 in the femoral tunnel 20 using the another attachment device 210 according to the invention. The bottom end 26 of the ligament replacement 22 is attached to the tibia 16 using the attachment device 10 as described above. The attachment device 210 as shown in FIG. 8 forms a two-part frustoconical clamp 230. The clamp 230 includes a first curved channel 232 having a wall 233 that terminates in a first longitudinal edge 234 and a second longitudinal edge 236. The wall 233 has a first semicircular end 237 and a second semicircular end 238 of greater radius than the first semicircular end 237. The clamp 230 also includes a second curved channel 242 having a wall 243 that terminates in a first longitudinal edge 244 and a second longitudinal edge 246. The wall 243 has a first semicircular end 247 and a second semicircular end 248 of greater radius than the first semicircular end 247. When the first edge 234 and the second edge 236 of the first channel 232 are brought into mating contact with the first edge 244 and the second edge 246 of the second channel 242 respectively, the clamp 230 has a hollow frustoconical shape. The first channel 232 and the second channel 242 can comprise the porous metallic materials mentioned above for clamp 30.

To use the attachment device 210, the ligament replacement 22 is positioned between the first channel 232 and the second channel 242, and the first edge 234 and the second edge 236 of the first channel 232 are brought near the first edge 244 and the second edge 246 of the second channel 242 respectively. The clamp 230 is then inserted into the femoral tunnel 20 with the first semicircular end 237 and the first semicircular end 247 going in first. The first channel 232 and the second channel 242 clamp the ligament replacement 22, and are wedged against the inner surface 19 of the femoral tunnel 20. The compression of the ligament replacement 22 allows for ingrowth of soft tissue into the first channel 232 and the second channel 242 and therefore the implant success rate increases.

Referring now to FIG. 9, there is shown a prior art femoral prosthesis 310 that may be implanted in a resected femur as part of a hip replacement procedure. The prosthesis 310 includes a body 312 having a neck portion 313, a femoral head 314 and a collar 315. The femoral head 314 is received in an acetabular component (not shown) that is mounted in a patient's pelvis as is well known in the art. Extending away from the body 312 of the prosthesis 310 is a generally cylindrical or tubular stem 316 that is inserted within the intramedullary canal of the femur 14. The stem 316 has an upper lateral corner 317. The femoral prosthesis 310 may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone).

Turning to FIGS. 10 and 11, another attachment device 410 according to the invention is shown. The prosthesis 310a is similar to the prosthesis 310 of FIG. 9. The prosthesis 310a includes a body 312a having a neck portion 313a, a femoral head 314a and a collar 315a. However, an indented section 420 of the upper lateral corner 417 of the prosthesis 310a has been removed. The attachment device 410 includes a clamp 430 having a convex tissue engaging surface 432, a generally rectangular periphery 434, a bottom surface 436, and throughholes 438 and 439. In the cross-section shown in FIG. 10, the clamp 430 has a general shape of a quadrant of an oval. The clamp 430 may comprise a material that promotes soft tissue ingrowth from the ligament replacement 22 into clamp 430. The clamp 430 can comprise the porous metallic materials mentioned above for clamp 30.

The attachment device 410 also includes fasteners such as screws 446, 447 that are inserted through the throughholes 438, 439, respectively, through the ligament replacement 22, and into the stem 316a of the prosthesis 310a. The screws 446, 447 compress the ligament replacement 22 between the convex tissue engaging surface 432 of the clamp 430 and the concave tissue engaging surface 442 of the indented section 420 of the stem 316a of the prosthesis 310a. The convex tissue engaging surface 432 of the clamp 430 has a first curvature is greater than the second curvature of the concave tissue engaging surface 442. This allows for varying degrees of ligament replacement 22 compression due to the difference in curvature of the first curvature of the convex tissue engaging surface 432 of the clamp 430 and the second curvature of the concave tissue engaging surface 442. Either end of the ligament replacement 22 can be attached to another bone or implant.

Figure 12:
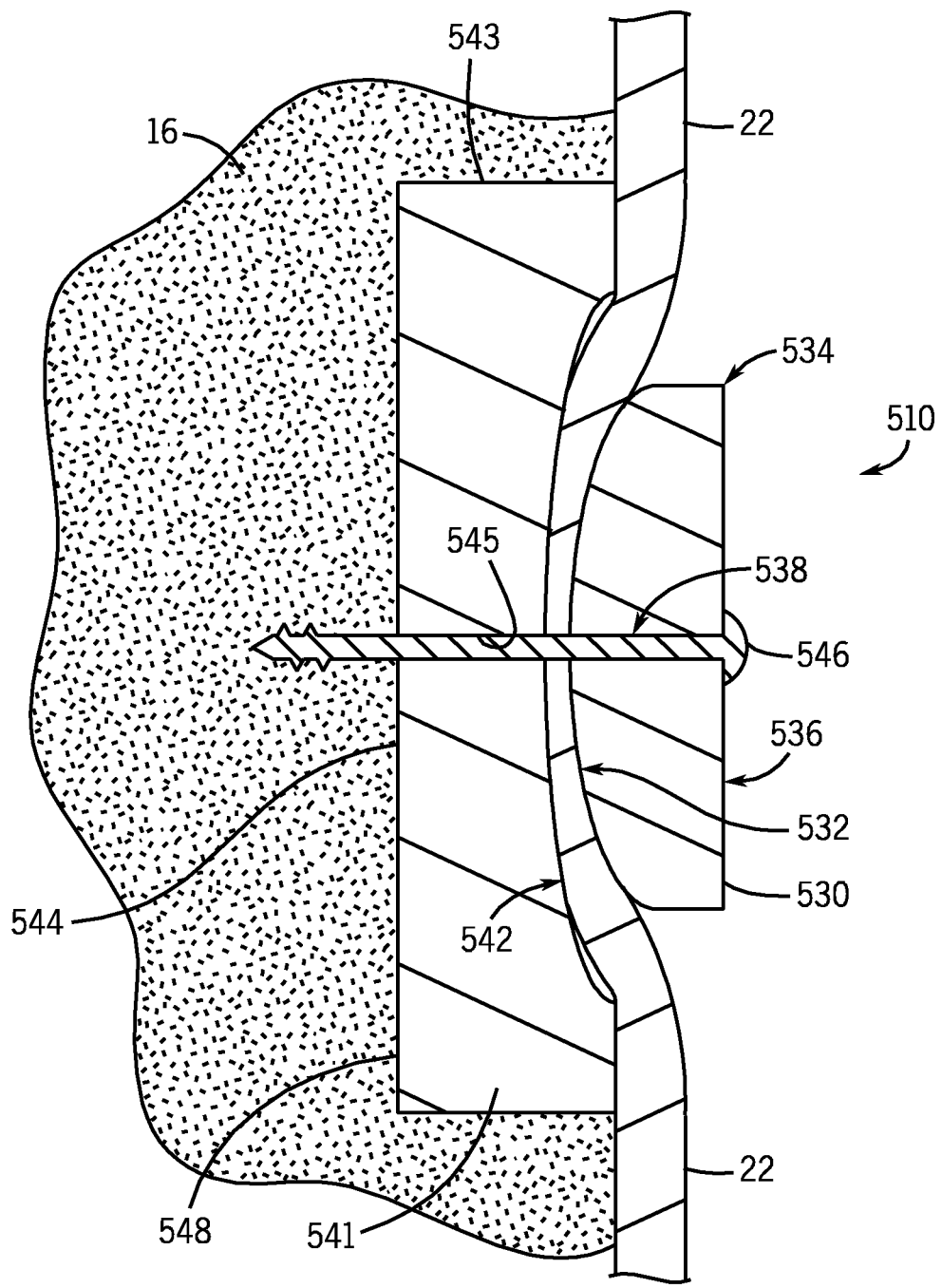
FIG. 12 is a detailed cross-sectional view similar to FIG. 2 showing still another version of an attachment device according to the invention.

Looking now at FIG. 12, there is shown another embodiment of an attachment device 510 according to the invention. The attachment device 510 includes a first clamp 530 having a domed (convex) tissue engaging surface 532, a circular periphery 534, a bottom surface 536, and a central throughhole 538. The attachment device 510 also includes a second clamp 541 having a concave tissue engaging surface 542 in a well, a circular periphery 543, a bottom surface 544, and a central throughhole 545. The attachment device 510 also includes a fastener such as screw 546 that is inserted through the throughhole 538, through the ligament replacement 22, through the throughhole 545, and into the tibia 16. The screw 546 compresses the ligament replacement 22 between the first clamp 530 and the second clamp 541, which can be inserted in a recess 548 formed in the tibia 16.

The tissue engaging surface 532 of the first clamp 530 has a first curvature which can be calculated as the inverse of the radius from a point (which is on the central axis of the throughhole 538 and which is in the plane of the bottom surface 536) to various points on the tissue engaging surface 532. The concave tissue engaging surface 542 of the second clamp 541 has a second curvature which can be calculated as the inverse of the radius from a point (which is on the central axis of the throughhole 538 and which is in the plane of the bottom surface 536) to various points on the concave tissue engaging surface 542 of the second clamp 541.

The first curvature of the convex tissue engaging surface 532 of the clamp 530 is greater than the second curvature of the concave tissue engaging surface 542 of the second clamp 541. This allows for varying degrees of ligament replacement 22 compression due to the difference in curvature of the first curvature of the convex tissue engaging surface 532 of the clamp 530 and the second curvature of the concave tissue engaging surface 542 of the second clamp 541. Note in FIG. 12 how the gap between the convex porous ingrowth surface 532 on one side and the concave tissue engaging surface 542 of the second clamp 542 on the other side gets bigger near the periphery 534 of the clamp 530 and is smallest centrally near screw 546. As tendons and ligaments are of different thicknesses and have different requirements for tension between the first clamp 530 and the second clamp 541, having varying degrees of compression between the first clamp 530 and the second clamp 541 increases the likelihood that at some point along the convex tissue engaging surface 532 of the first clamp 530 and the concave tissue engaging surface 542 of the second clamp 541, the level of compression would be optimal for ingrowth of soft tissue and therefore implant success rates increase.

The first clamp 530 and the second clamp 541 may comprise a material that promotes soft tissue ingrowth from the ligament replacement 22 into first clamp 530 and the second clamp 541 The first clamp 530 and the second clamp 541 can comprise the porous metallic materials mentioned above for clamp 30.

Thus, the invention provides methods and devices for the attachment of a tendon or ligament structure to bone and/or a prosthetic implant (such as a joint replacement device). In particular, the methods and devices use a clamping strategy employing soft tissue healing to a porous metal clamp.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A device for attaching soft tissue to a bone or a prosthetic implant, the device comprising:
    a clamp comprising a porous metallic material, the clamp including a first surface, a convex tissue engaging surface opposite the first surface, and a throughhole extending from the first surface to the convex tissue engaging surface; and
    a fastener dimensioned for placement in the throughhole, the fastener being dimensioned to engage a surface of the clamp, the soft tissue and the bone or the prosthetic implant such that the soft tissue is compressed between the tissue engaging surface and the bone or the prosthetic implant,
    wherein the convex tissue engaging surface of the clamp has a first curvature, the bone or the prosthetic implant includes a depression of a second curvature, and the first curvature is greater than the second curvature, and
    wherein the clamp is configured such that a gap between the tissue engaging surface of the clamp and a concave surface of the depression of the bone or the prosthetic implant is bigger near a periphery of the clamp and smaller centrally near the fastener when the soft tissue is compressed between the tissue engaging surface and the bone or the prosthetic implant, and
    wherein the clamp is adapted to compress the soft tissue between the tissue engaging surface of the clamp and the concave surface of the depression of the bone.

2. The device of claim 1 wherein:
the convex tissue engaging surface includes a raised section around the throughhole.

3. The device of claim 1 wherein:
the clamp includes a periphery having a shape selected from circular, rectangular, elliptical and oval.

4. The device of claim 1 wherein:
the porous metallic material comprises tantalum.

5. The device of claim 1 wherein:
the convex tissue engaging surface of the clamp is dome shaped.

6. A device for attaching soft tissue to a bone or a prosthetic implant, the device comprising:
    a first clamp comprising a porous metallic material, the first clamp including a first surface, a convex tissue engaging surface opposite the first surface, and a throughhole extending from the first surface to the convex tissue engaging surface;
    a second clamp comprising a porous metallic material, the second clamp including a first surface, a concave tissue engaging surface opposite the first surface, and a throughhole extending from the first surface to the concave tissue engaging surface; and
    a fastener dimensioned for placement in the throughhole of the first clamp and the throughhole of the second clamp, the fastener being dimensioned to engage a surface of the first clamp, the soft tissue and the bone or the prosthetic implant such that the soft tissue is compressed between the convex tissue engaging surface of the first clamp and the concave tissue engaging surface of the second clamp,
    wherein the convex tissue engaging surface of the first clamp has a first curvature, the concave tissue engaging surface of the second clamp has a second curvature, and the first curvature is different from the second curvature.

7. The device of claim 6 wherein:
the first curvature is greater than the second curvature.

8. The device of claim 6 wherein:
the first clamp includes a periphery having a shape selected from circular, rectangular, elliptical and oval, and the second clamp includes a periphery having a shape selected from circular, rectangular, elliptical and oval.

9. The device of claim 6 wherein:
the device is for attaching soft tissue to a bone, and the second clamp is adapted to be received in a depression in the bone.

10. The device of claim 6 wherein:
the porous metallic material of the first clamp comprises tantalum, and
the porous metallic material of the second clamp comprises tantalum.

11. The device of claim 6 wherein:
the convex tissue engaging surface of the first clamp is dome shaped.

* * * * *